United States Patent
Bruce et al.

(10) Patent No.: US 6,565,606 B1
(45) Date of Patent: May 20, 2003

(54) IMPLANT, METHOD OF MAKING THE SAME AND USE THE SAME

(75) Inventors: Lars Bruce, Viken (SE); Ingrid Bruce, Viken (SE)

(73) Assignee: Lanka Limited, Douglas (GB)

( * ) Notice: Subject to any disclaimer, the term of this patent is extended or adjusted under 35 U.S.C. 154(b) by 0 days.

(21) Appl. No.: 09/786,755

(22) PCT Filed: Sep. 9, 1999

(86) PCT No.: PCT/SE99/01576

§ 371 (c)(1),
(2), (4) Date: May 24, 2001

(87) PCT Pub. No.: WO00/13615

PCT Pub. Date: Mar. 16, 2000

(30) Foreign Application Priority Data

Sep. 9, 1998 (SE) .............................................. 9803078

(51) Int. Cl.⁷ .................................................. A61F 2/28
(52) U.S. Cl. ................................ 623/23.63; 623/23.52; 623/16.11
(58) Field of Search .......................... 623/16.11, 17.11, 623/17.12, 17.17, 17.18, 18.11, 23.52, 23.63

(56) References Cited

U.S. PATENT DOCUMENTS

| | | | |
|---|---|---|---|
| 4,430,760 A | * 2/1984 | Smestad | |
| 4,501,269 A | 2/1985 | Bagby | 128/92 |
| 4,657,548 A | * 4/1987 | Nichols | |
| 4,755,184 A | 7/1988 | Silverberg | 623/16 |
| 4,787,906 A | * 11/1988 | Haris | |
| 5,015,247 A | 5/1991 | Michelson | 606/61 |
| 5,015,256 A | 5/1991 | Bruce et al. | 623/18 |
| 5,217,496 A | 6/1993 | Bruce et al. | 623/16 |
| 5,489,308 A | 2/1996 | Kuslich et al. | 623/17 |
| 5,549,679 A | 8/1996 | Caldarise | 623/22 |
| 5,571,189 A | 11/1996 | Kuslich | 623/17 |
| 5,660,225 A | * 8/1997 | Saffran | |
| 5,665,120 A | 9/1997 | Ohtsuka et al. | 623/16 |
| 5,676,699 A | * 10/1997 | Gogolewski et al. | |
| 5,676,700 A | 10/1997 | Black et al. | 623/16 |
| 5,863,297 A | * 1/1999 | Walter et al. | |
| 5,888,220 A | * 3/1999 | Felt et al. | |
| 5,919,234 A | * 7/1999 | Lemperle | |
| 6,022,376 A | * 2/2000 | Assell et al. | |
| 6,110,211 A | * 8/2000 | Weiss | 623/23.11 |
| 6,248,110 B1 | * 6/2001 | Reiley et al. | 606/93 |
| 6,409,764 B1 | * 6/2002 | White et al. | 623/16.11 |

FOREIGN PATENT DOCUMENTS

| | | |
|---|---|---|
| EP | 0 709 070 | 1/1996 |
| GB | 2 259 252 | 10/1993 |

\* cited by examiner

*Primary Examiner*—Ralph A. Lewis
(74) *Attorney, Agent, or Firm*—Smith, Gambrell & Russell

(57) ABSTRACT

An implant (prosthesis) comprising a batch of a mixture of porous grains/granular material of tissue-compatible type and disintegrated tissue-compatible biological material (preferably endogenous material, such as bone meal). The batch further comprises a component which allows moulding or modelling of the batch, and the batch is enclosed in a pouch or wrap made of a flexible tissue-compatible material and having pores/apertures/perforations or the like of a size which allows outgrowth and ingrowth of tissue of the biological material. The implant is applicable in many contexts, such as a fixing agent for a hip-bone prosthesis, as a filler in plastic surgery and as a bone growth promoting agent when treating rheumatism.

37 Claims, 1 Drawing Sheet

IMPLANT, METHOD OF MAKING THE SAME AND USE THE SAME

FIELD OF THE INVENTION

Figure 1:
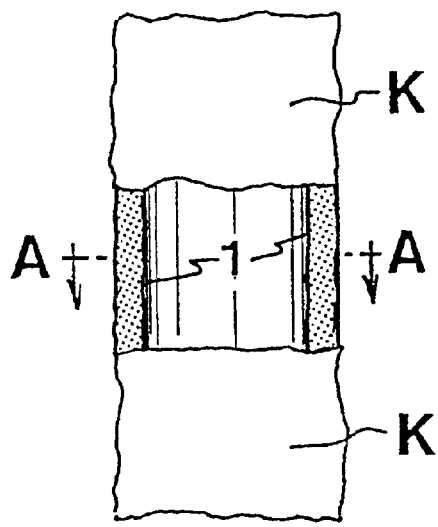

The present invention relates to an implant and a method of making the same and use of the same.

BACKGROUND

U.S. Pat. No. 5,217,496 (Bruce) discloses an implant (prosthesis) comprising a layer of a mixture of pulverulent material of tissue-compatible type and disintegrated tissue-compatible biological material which, by adding a nutrient solution, has been allowed to grow and link the components of the mixture to each other. This patent publication also discloses a method of making such an implant using a mould.

U.S. Pat. No. 5,015,256 (Bruce) discloses a means for fixing in a cementless manner a joint prosthesis, comprising a biological compatible granular material of essentially irregular, porous and plastic grains having a size of less than 5 mm. For fixing of the joint prosthesis, the means is inserted into the cavity in which the prosthesis is to be fixed, and the prosthesis is driven into the means and the cavity during vibration of the grains. The vibration causes the grains to be packed in the cavity between prosthesis and cavity wall during interlocking and locking of the prosthesis in the cavity. The mass or bed of the material may contain grains of endogenous material.

Experiments carried out using the above-described fixing technique have proved that a particularly quick and stable, permanent and painless fixing (healing) of prosthesis is achieved precisely if the granular material comprises endogenous material formed of tissue of the same type in/against which the implant is to be inserted or placed, respectively, for instance bone tissue from the femoral cavity if the prosthesis to be fixed is a femoral prosthesis. The bone tissue forms bone (cells) enclosing the grains and extending from the wall of the cavity to the prosthesis. Moreover, these experiments have shown that the more linked grains of material (plus endogenous material), the quicker fixing of the prosthesis. It seems as if the tendency of the body cells to grow increases the shorter the distance between the grains.

The invention is based on the teachings of the known techniques as described above and of the above-mentioned experiments. The knowledge on which the invention is based thus is that the grains of material must be linked to each other and preferably compacted, and that endogenous biological material, tissue, and nutriment should be available in the material or should have the possibility of penetrating the same.

One could say that the body cavity in U.S. Pat. No. 5,015,256 constitutes the mould in the method according to U.S. Pat. No. 5,217,496 and comprises natural nutrient solution for cell growth, viz. endogenous body fluid, such as blood.

U.S. Pat. No. 4,755,184 discloses an implant in the form of a sausage, the casing of which consists of a porous hose tied at the ends and containing hydroxyapatite. The casing is firmly packed.

INVENTION DESCRIPTION

According to the invention, the implant comprises a batch of a mixture of porous grains/granules of tissue-compatible type and of disintegrated tissue-compatible biological material, preferably endogenous tissue and preferably endogenous tissue from the location of the implant, said batch further comprising one more component which makes the batch capable of being moulded or modelled, said batch being enclosed in a pouch or a wrap of a tissue-compatible, flexible sheet, foil, woven fabric, or the like with apertures/perforations/meshes which are permeable for tissue growth from inside the pouch/wrap to the surroundings and from outside into the pouch. The batch must be well kept together and preferably compacted in the pouch/wrap. The latter should be closed, for example sewn together so that no grains/granules can leave the pouch/wrap. The pouch/wrap may consist of, for instance, gauze bandage.

The preferably performed packing of the batch in the pouch/wrap is carried out to a degree of packing which is necessary for the purpose of the implant. If the purpose of the implant is to support parts of the body or keep a distance between parts of the body, such as vertebrae, the degree of packing g must be greater, i.e. be capable of having a supporting and spacing function, than in the case where it is a matter of filling a cavity in the body, such as for plastic surgical purposes, and other purposes if it is a matter of bone growth promoting agent for rheumatics.

The compacting of the batch in the pouch/wrap can advantageously be performed by vibration. Vibration produces the further advantage that the components of the batch are adequately mixed and that nutrient penetrates into the pores of the grains/granules, which is advantageous. Vibration can take place at a certain higher frequency for mixing and another lower frequency for compacting. For vibration, use can be made of e.g. ultrasound.

Nutrient can be added to the batch in vitro, for example by lowering the pouch with the batch into a conventional nutrient solution or blood/plasma and vibrating the pouch, through the wall apertures of which the nutrient reaches the batch to provide tissue growth. However, nutrient can also be added to the batch in vivo, at the location of the implant, which then contains endogenous fluids which can penetrate the pouch.

According to the purpose of application, the implant can be sewn, nailed etc. to the location of the implant in/on the body, which can be necessary when the implant fills a cavity in the body and there is a risk of dislocation. However, if the implant can be expected to be fixed by wedging, such as between vertebrae, no specific fixing means need be used.

The implant is formed during compacting to a shape which well fills the cavity, the space or the distance where it is to be inserted. This is important since otherwise (distance between body tissue and pouch) there is a risk that the implant does not grow on or that connective tissue forms between pouch and body tissue.

It would have become apparent that the shape of the implant according to the invention may be arbitrary, such as a flat plate, a piece of strip, a cylinder, a rod etc.

The pouch containing said mixture can be shaped by using a further/some further tissue-compatible components in the batch which make the batch kneadable and retain the shape of the pouch/wrap caused by the kneading. A suitable component is a hardenable two-component fibrin adhesive which is available on the market, such as from IMMUNO (Schweiz) AG. A further suitable component is FocalSeal (registered trademark), a surgical sealing agent marketed by Focal, Inc. USA. However, it should be emphasised that blood (which contains fibrin and coagulates) in itself is a suitable further component which allows moulding of the mixture in or outside the pouch/wrap to the form of a cavity, to the form of which the implant is to be fitted. As a pattern for the moulding or modelling, use can be made of, for example, an X-ray recording of the body cavity in question.

When considered convenient, the pouch/wrap may be made of a resorbable material. One example is SURGICEL (™) from ETHICON LTD.

As material for the tissue-compatible grains/granules, it is possible to select according to the invention first of all titanium, but also other materials are suited, which are known to the skilled person for the purpose, such as bioceramics, bioglass, hydroxyapatite, polymers, dextran. Porous grains/granules which are not porous by nature, such as titanium, are obtained in prior-art manner by blowing gas or liquid through a melt of the material.

The grains/granules have an essentially uniform particle size distribution, preferably plastic and irregular. The reason for this is that, when interlocking and compacting by vibration, different particle sizes should not be arranged in layers in the body cavity with the ensuing risk of irregular and thus impaired tissue growth. By an essentially uniform particle size distribution is meant that the grain/granule diameter may vary by ±50%, preferably by ±25% or less. The absolute size of the grains/granules may vary in relatively wide ranges, a grain/granule size below 5 mm being considered most convenient. The lower limit may be difficult to establish, and it would be possible to use very small grain particles in combination with a biocompatible liquid which forms the small particles (dust). However, grains/granules above 0.1 mm are normally used. Preferably, the upper limit may be about 2 mm and the lower limit 0.5 mm. It may be generally said that the grain/granule size is selected in consideration of the space which after completed surgery should be packed with grains/granules, i.e. larger grains/granules can be selected for larger body cavities than for small ones. The terms "grains/granules", "irregular" and "diameter" cover other forms than (approximately) spherical.

If the implant according to the invention is to be used for replacement or repair of bone tissue, the grains/granules most preferably consist of plastic or not essentially elastic, continuously porous biocompatible material, preferably metal or metal alloy, such as titanium, having the following porosity characteristics:

the porosity is continuous the opening of pits/indentations/pockets and the channels/passages interconnecting the same has a width of >about 50 µm for bone tissue. Such a porosity results in voids in the grains which are interconnected by channels, passages, so that growth of bone tissue to a part of the outer surface of the grains allows the growth to continue through individual grains and out through other parts of the outer surface of the grains.

According to the invention, the mixing of the batch components to provide the above-mentioned batch can be carried out before introducing the batches into the pouch or before wrapping the batches. In this connection, a batch of nutrient is added to the mixture. Alternatively, and still according to the invention, the mixing can be carried out after introduction into the pouch or after wrapping the batches.

In, for instance, surgery on the spinal column for replacing worn-out intervertebral discs between vertebrae, use is often made of implants that are screwed between the vertebrae. Such implants are rigid and may contain bone fragments, see U.S. Pat Nos. 4,501,269 and 5,489,308. Such bone fragments are, however, not available in a sufficient quantity, and it is the implants that have the supporting function and may cause pain. Such implants are also complicated and expensive to manufacture.

The invention remedies this and suggests an implant of the type described above for stabilising the spinal column.

DRAWING DESCRIPTION

Figure 1A:
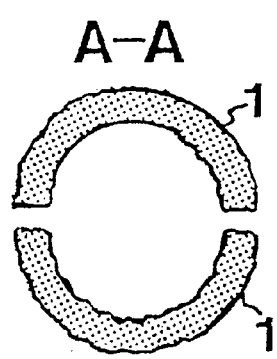

FIG. 1 is a schematic view of two annular-cylindrical pouches 1 having contents as described above and being inserted between two vertebrae K. The pouches 1 are well filled with the batch (the grains/granular material is made of titanium), which has been vibrated for adequate mixing and compacting so that the distance between the vertebrae can be kept correct. Bone forms rapidly and takes over the supporting function. The pouches are made of the above-described, exemplifying resorbable material. FIG. 1a is a sectional view a—a.

Figure 2:
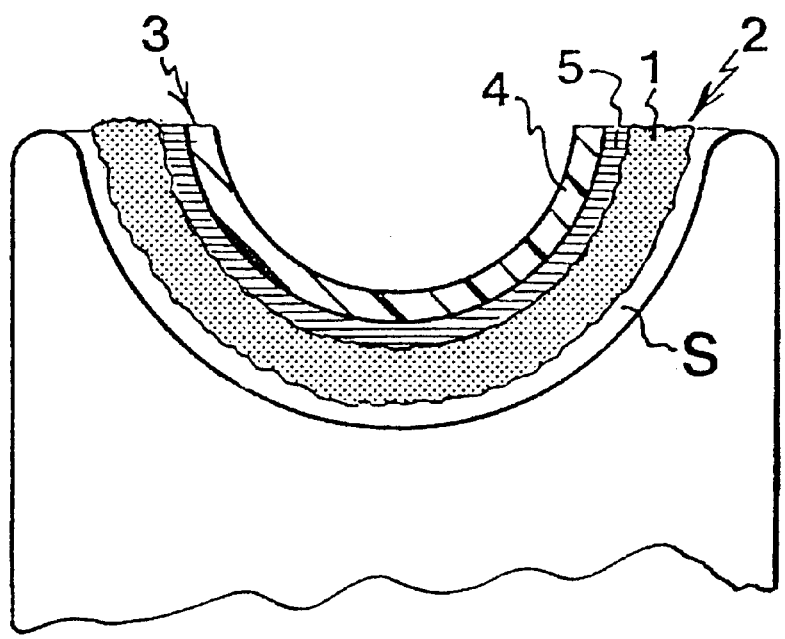

FIG. 2 illustrates an implant 2 according to the invention inserted in a hip-bone cavity S for fixing a hip-bone implant 3 in the hip-bone cavity, said hip-bone implant 3 consisting of a conventional plastic cup 4 coated with titanium 5 and resting on, with a press fit, a thin pouch 1 formed according to the hip-bone cavity and containing the above-described batch in which the grains/granules consist of titanium. The pouch 1 is also made of the described, exemplifying resorbable material in the form of a woven fabric.

In one more embodiment of the invention, the interior chamber in a spinal column implant is of the type described in, for instance, U.S. Pat. Nos. 5,015,247 and 4,501,269 filled with an implant according to the invention.

What is claimed is:

1. An implant, comprising:
   a mixture of tissue-compatible porous particulate material, of tissue-compatible biological material and of a modeling or molding tissue-biocompatible component; and a pouch or wrap in which the mixture is contained, and said pouch or wrap being made of a flexible tissue-compatible material and having openings of a size which allows ingrowth and outgrowth of tissue of the biological material.

2. An implant as claimed in claim 1, wherein the flexible material is a resorbable material.

3. An implant as claimed in claim 1, wherein the porous particulate material is selected from the group consisting of titanium, polymer and dextran.

4. An implant as claimed in claim 1, wherein the mixture further comprises a nutrient that promotes growth of the tissue-compatible biological material in the mixture.

5. An implant as claimed in claim 1, wherein said modeling or molding component comprises a hardenable component and a hardening agent therefor.

6. An implant as claimed in claim 1, wherein the modeling or molding, component is blood.

7. An implant as claimed in claim 1, wherein the porous material comprises grains or granules sized from 0.1 to 5 mm.

8. An implant as claimed in claim 1, wherein the mixture is maintained in a compacted state by the pouch or wrap enclosing said mixture.

9. An implant as claimed in claim 1, wherein the porous material has the following porosity characteristics:

the porosity is continuous the opening of pits, indentations or pockets and the channels or passages interconnecting the same has a width of >about 50 µm for bone tissue.

10. A method of forming an intervertebral prosthesis comprising utilizing the implant of claim 1 as, or as a component of, the intervertebral prosthesis.

11. A method of forming a hip-joint prosthesis comprising providing a hip-joint prosthesis component and utilizing the implant of claim 1 as a fixing agent for said hip-joint prosthesis component.

12. A method of carrying out plastic surgery which comprises utilizing the implant of claim 1 as a filler in the plastic surgery.

13. A method of providing a bone growth promoting agent for treating rheumatism, comprising providing the implant of claim 1 as a bone growth promoting agent for use in treating rheumatism.

14. A method of filling in body cavities, pits, indentations or carrier areas between parts of the body comprising utilizing the implant of claim 1 as a filler material.

15. A method of forming a spacer for use as a spacer in a body, comprising manipulating the implant of claim 1 to form a desired shape so as to provide a spacer suited for receipt in a spacer cavity in the body.

16. A method of reinforcing a body region with defective or removed tissue, comprising positioning the implant of claim 1 in a reinforcing position relative to the body region.

17. A method of replacing bone tissue comprising providing the implant of claim 1 as a bone replacement material.

18. A method of providing a body implant comprising positioning the implant of claim 1 in a body implant position.

19. An implant as claimed in claim 1 wherein said biological material comprises an endogenous material.

20. An implant as claimed in claim 1 wherein said biological material comprises a bone material.

21. An implant as claimed in claim 1 wherein said porous material comprises particles of a size above 0.1 mm, and wherein said particles have a particle size distribution which is uniform in varying by 25% or less.

22. An implant as recited in claim 1 wherein said pouch or wrap is a closed container enclosing a body of said mixture and said pouch is of a material sufficiently flexible to accommodate kneading of the pouch or wrap.

23. An implant as recited in claim 1 wherein the porous material comprises grains or granules of from 0.5 to 2 mm in size.

24. An implant as recited in claim 1 wherein said porous material comprises a metal or metal alloy material.

25. An implant as recited in claim 1 wherein said biological material comprises an endogenous material formed of a tissue of a common type as tissue in which the implant is to located in or against.

26. An implant as recited in claim 25 wherein said endogenous material comprises particles of femoral cavity bone tissue and said implant forms a femoral prosthesis structure.

27. An implant as recited in claim 1 wherein said pouch or wrap is a woven fabric.

28. An implant as recited in claim 1 wherein said pouch or wrap is of a regenerated cellulose or polymer material.

29. An implant as claimed in claim 1, wherein said modeling or molding tissue-biocompatible component of the mixture also provides a nutrient that promotes growth of the tissue-compatible biological material in the mixture.

30. An implant as claimed in claim 1 wherein said modeling or molding tissue-biocompatible component of the mixture is a material that contains fibrin and coagulates.

31. An implant as claimed in claim 30 wherein said modeling or molding tissue-biocompatible component is blood which is provided to the mixture in vitro.

32. An implant as claimed in claim 30 wherein said modeling or molding tissue-biocompatible component is blood which is provided to the mixture in vivo.

33. An implant as recited in claim 1 wherein said modeling or molding tissue-biocompatible component comprises a surgical sealing agent.

34. An implant, comprising:
   a mixture of tissue compatible porous granular material, of tissue compatible biological particles, and of a further tissue compatible mixture molding material; and
   a pouch which receives said mixture and is formed of a flexible porous material having pores which permit growth of tissue through the pouch while containing the granular material.

35. An implant as claimed in claim 34, wherein said molding material comprises a hardenable component and a hardening agent therefore.

36. An implant as claimed in claim 34, wherein said molding material comprises a surgical sealing agent.

37. An implant as claimed in claim 34, wherein said molding material comprises blood.

* * * * *